(12) United States Patent
Griech et al.

(10) Patent No.: US 6,319,359 B1
(45) Date of Patent: Nov. 20, 2001

(54) PROCESS FOR QUANTITATIVELY DETECTING CONSTITUENTS OF A PULP/FLUID MIXTURE

(75) Inventors: Wolfgang Griech, Heidenheim; Rudolf Münch, Königsbronn; Franz Winter, Lorch, all of (DE)

(73) Assignee: Voith Sulzer Papiertechnik Patent GmbH, Heidenheim (DE)

( * ) Notice: Subject to any disclaimer, the term of this patent is extended or adjusted under 35 U.S.C. 154(b) by 0 days.

(21) Appl. No.: 09/318,810

(22) Filed: May 26, 1999

(30) Foreign Application Priority Data

May 27, 1998 (DE) .............................. 198 23 695

(51) Int. Cl.[7] ........................................ D21C 7/12
(52) U.S. Cl. .............. 162/49; 162/50; 162/192; 162/198
(58) Field of Search .............. 162/49, 50, 162, 162/192, 199

(56) References Cited

U.S. PATENT DOCUMENTS

| 5,491,340 | 2/1996 | Saarinen ........................ 250/339.06 |
| 5,638,284 | 6/1997 | Helmer et al. .................. 364/471.01 |
| 5,841,671 | 11/1998 | Furumoto ...................... 364/471.01 |

FOREIGN PATENT DOCUMENTS

| 3706458 | 9/1988 | (DE) . |
| 3712879 | 11/1988 | (DE) . |
| 4133439 | 4/1992 | (DE) . |
| 4206532 | 9/1993 | (DE) . |
| 4422400 | 1/1996 | (DE) . |
| 19510008 | 9/1996 | (DE) . |
| 29709504 | 9/1997 | (DE) . |
| 19611931 | 10/1997 | (DE) . |
| 19613985 | 11/1997 | (DE) . |
| 0619485 | 10/1994 | (EP) . |
| 82/03688 | 10/1982 | (WO) . |
| 95/08019 | 3/1995 | (WO) . |
| 95/29396 | 11/1995 | (WO) . |

OTHER PUBLICATIONS

U. Kasurinen, "Wochenblatt für Papierfabrikation" [Paper Manufacturing Weekly], No. 7, pp. 272–279, Münich (1996).
C. Sklarczyk et al., "Schichten Charakterisieren," *Materialprüfung*, vol. 40, pp. 149–153 (1998).
Patent Abstract of Japanese Patent No. 03 238845, published on Oct. 24, 1991.
Patent Abstract of Japanese Patent No. 03 238345, published on Oct. 24, 1991.

*Primary Examiner*—Dean T. Nguyen
(74) *Attorney, Agent, or Firm*—Greenblum & Bernstein, P.L.C.

(57) ABSTRACT

Process and measurement device for quantitatively detecting constituents of a pulp/fluid mixture for paper and/or cardboard production. The device includes at least one radiation source for irradiating the mixture in a number of definite, different wavelength ranges. The device also includes at least one sensor for measuring the intensity of radiation that has been influenced by the mixture, and at least one set of measurement electronics. Each sensor detects only one of the definite, different wavelength ranges of the radiation at a particular time. The process includes irradiating the mixture with at least one radiation source, the irradiation occurring in a number of definite, different wavelength ranges; and measuring the intensity of radiation that has been influenced by the mixture by at least one sensor. Each sensor detects only one of the definite, different wavelength ranges of the radiation at a particular time. The measurement device is adaptable for use in sections of a pulp density regulated headbox of a paper making machine, in inflows and/or outflows of a vat belonging to a paper machine or part thereof, in a region of a wet section of a paper machine, and in white water of a paper machine.

22 Claims, 1 Drawing Sheet

PROCESS FOR QUANTITATIVELY DETECTING CONSTITUENTS OF A PULP/FLUID MIXTURE

CROSS REFERENCE TO RELATED APPLICATION

The present application claims priority under 35 U.S.C §119 of German Patent Application No. 198 23 695.6, filed on May 27, 1998, the disclosure of which is expressly incorporated by reference herein in its entirety.

BACKGROUND OF THE INVENTION

1. Field of the Invention

The invention relates to a process and a measurement device for quantitatively detecting constituents of a pulp/fluid mixture for paper or cardboard production and a process of using the measurement device.

2. Background and Material Information

A number of conventional processes and measurement devices for quantitatively detecting constituents are described in "Wochenblatt für Papierfabrikation", Paper Manufacturing Weekly, No. 7, 1996, pp. 272 to 279. According to the conventional processes and measurement devices, pulp consistency measurements (percentage of total mass) in a consistency range of 1.5% and higher have been carried out based upon shear force measurements and measurement of a dielectric constant over the propagation speed of microwaves. Pulp consistency measurements in the low consistency range below 1.5% are carried out, among other ways, based upon a depolarization measurement. Polarized light is conveyed through a pulp suspension, whereupon the polarized and depolarized portions in the measured light are compared to each other.

A measurement device is also described which, for various wavelengths, measures the depolarization of emitted laser light, the damping and backscattering of laser and xenon light, and the absorption of xenon light. As a result, fifteen different optical measurement values are registered simultaneously. The fibrous solids and filler consistencies are calculated from these measurement values. The obtained depolarization signal of the penetrating light is representative of the overall consistency. Damping and backscattering are used to determine the filler consistency and the overall consistency. This known measurement device is particularly useful for optimizing a wet section. This device is able to detect a number of different constituents of the mixture. However, it is relatively complicated and thus expensive. In addition, transmitted light is a prerequisite, which involves a greater space requirement. Further, the measurement conduit must have a small diameter, especially when the pulp consistency increases. At higher pulp consistencies, the medium must be diluted.

For measurements in the low consistency range, a known device utilizes the peak value measurement method with transmitted light, wherein fibers are counted by a focused light beam and the ash content is measured by absorption. This known device can distinguish ash and fibers as a group, but is incapable of further differentiation. Moreover, transmitted light is used, thus requiring additional space. Also, the measurement conduit must have a relatively small diameter, particularly when the pulp consistency increases. Finally, at higher pulp consistencies, the medium must be diluted.

SUMMARY OF THE INVENTION

The present invention creates an improved process and an improved measurement device for quantitatively detecting constituents of a pulp/fluid mixture in which the disadvantages mentioned above are eliminated.

According to the invention, the process includes irradiating a mixture by at least one radiation source that irradiates in a number of definite, different wavelength ranges. The intensity of radiation that has been influenced by the mixture is measured by at least one sensor, each sensor measuring only one of the definite, different wavelength ranges of the radiation at a particular time. A spectrometer is therefore not required.

In this connection, radiation that has been reflected by the mixture can advantageously be detected by at least one sensor. In addition to this or alternatively, it is possible to detect radiation that has passed through the mixture by the one sensor. Detecting only radiation that has been reflected by the mixture provides the advantage of a low space requirement. A sensor can, for example, be attached to a container of the mixture, which is suspended.

In an embodiment of the invention, the mixture is irradiated by at least one optical radiation source and the intensity of the optical radiation that has been influenced by the mixture is measured by at least one photoelectric sensor. If the mixture is irradiated by a number of radiation sources of different wavelength ranges, then it is advantageous if the mixture is irradiated in chronological sequence by the individual different radiation sources and/or by different combinations of radiation sources.

In an embodiment of the present invention, a wide band sensor is used, which includes all of the different wavelength ranges. Because only one of the different wavelength ranges of the radiation is detected at one time, a spectrometer is not required.

In a particular embodiment, at least one LED is used as a radiation source, which is particularly advantageous in view of the LED's longevity and low cost. Consequently, a longstanding belief that LEDs are not suitable can be overcome.

In a wavelength range from 1300 to 2400 nm for which LEDs are not available, there are relatively pronounced peaks in the absorption spectrum, e.g., at 1450 nm water harmonic, 1930 nm water, 2100 nm cellulose fiber, 2010 nm clay, approx. 2300 nm latex and lignin, 2300 to 2400 nm polyethylene and other plastics. Thus, up to now lamps with incandescent filaments have been used. However, trials have shown that the constituents of the mixture can also easily be inferred using a number of LEDs having different wavelengths. Thus, the relative measurement precision, i.e., the response sensitivity of a sensor to very slight consistency fluctuations, is very high. A possible slight limitation of the absolute measurement precision is therefore insignificant. The considerably higher service life of LEDs in comparison to lamps with filaments is also particularly advantageous. This is particularly crucial for use in a dilution water headbox where 50 to 150 sensors are typically used simultaneously and the operator cannot reasonably be expected to continuously contend with lamp failures.

An additional inference from the absorption of different wavelengths is possible if at least two sensors are used, the sensors being disposed at different distances from the radiation sources. Fundamentally, it is also possible to associate each radiation source with its own sensor or its own pair of sensors. In this regard, more space is required. However, the fact that the measurement results obtained by the sensors can be queried simultaneously is advantageous.

The radiation sources can, for example, also be provided in a common container. Therefore, the radiation sources can be practically produced as a single radiation source, for example as a lamp with a number of different filaments. Thus, the type of radiation respectively emitted can then be changed, particularly as a function of electrical input signals.

The radiation sources and sensors can be separated from the mixture by a window. Alternatively, it is conceivable for there to be a coupling by way of a system of mirrors or fiber optic cables made of glass or plastic. The structural cost in this embodiment is somewhat greater, but it saves space.

In an exemplary embodiment, three optical radiation sources and two sensors are used. As a result, six signals are available. The required hardware can be simply integrated, for example, into a pulp density regulated headbox. It requires little space in the machine and can be produced very inexpensively.

According to the exemplary embodiment, an infrared LED (e.g., 880 nm or 950 nm), a red LED (e.g., 635 nm), and a blue LED (e.g., 480 nm, possibly a gallium nitrite LED with 430 nm) are used. The angle of radiation of the LEDs is crucial to the measurement process. At least one LED is advantageously used having an angle of radiation between approximately 12° and approximately 30°.

The switching frequency of the LEDs should be high in comparison to the time pattern in which the consistency values are required. This switching frequency is limited by the limit frequencies of the sensors and the LEDs as well as by the speed of the evaluation electronics. In actual use, for example, it is conceivable for there to be approximately 1000 or more switching events per second. It is therefore possible, for example, to obtain a consistency measurement value every 0.5 seconds, which has in turn been produced from the evaluation of more than 500 individual measurements. The same result can also be achieved, for example, by virtue of the fact that a switching frequency of 50 Hz is selected and ten individual measurement values are taken after each switching event.

The most important constituents of the mixture can be inferred from the measurement values obtained, for example by a comparison with experimental values. It has also turned out that a general consistency change has approximately the same effect in all measurement signals, while a change of the type of pulp has very different effects on these signals. Experiments can be used to test how a change, for example in the ash concentration, the fiber concentration, and/or the overall concentration is reflected in the measurement signals. Additional information, for example regarding the homogeneity of the mixture, can be inferred from the statistical properties of the multitude of individual measurements.

The relevant information is suitably inserted into a corresponding evaluation algorithm. This algorithm is then used in relevant control and/or evaluation electronics to determine the quantity of the different constituents from the measurement signals.

The experiments include putting stock into a mixing chamber, for example, 0.5% into ten liters; recording six raw measurement signals; adding a minimum amount of water, for example, 0.1 liter, and recording six raw measurement signals. Adding the water and recording the measurement signals is repeated several times. Then, all of the data is inserted into a list and the consistency is calculated based upon the initial consistency and the added water. Then, the coefficients $a_i$ (best fit) are calculated according to equation (1)

$$(1) Y = a_0 + a_1 X_1 + \ldots + a_6 X_6 + a_7 X_1^2 + \ldots + a_{12} X_6^2 + \ldots$$

In other words, $a_i$ is calculated by using the known partial least squares method. Y represents the calculated consistency and $X_i$=the raw measurements.

In another exemplary embodiment, the intensity of optical radiation that has been influenced by the mixture is measured at the same time as a dielectricity measurement and a ray-based absorption measurement is carried out. In this embodiment, the measurement of the radiation intensity, the dielectricity measurement, and the ray absorption measurement are used for quantitatively detecting constituents of the mixture. For the dielectricity measurement, the mixture can be subjected to microwave radiation. Optical radiation, in particular an infrared radiation or visible light, is once more used for the intensity measurement.

The simultaneous measuring is similar to the experimenting explained above except that instead of six raw signals, more signals are used. For example, eight, including absorption of ray and dielectricity measurements. To measure constituents, known amounts of ash and/or fibers are added whenever the water is added as described above.

In another embodiment, a number of sensors having different spectral sensitivities are used. In this instance, the mixture is preferably irradiated by a single radiation source. For example, at least one sensor/filter unit can be used having spectral sensitivity and/or permeability that can be adjusted. The respective adjustments can be carried out, for example, as a function of electrical input signals. The filter is provided for noise reduction and is preferably a moving average filter that averages over a 50 millisecond time period.

In the exemplary embodiment, optical radiation that has been influenced by the mixture is spectrally divided on the sensor end and is then conveyed to a photodiode array that preferably includes at least 16 and optimally 256 sensors. For example, a monolithic array of 256 sensors can be used. When 256 spectral lines are used, the amount of information received is considerable, enabling a significantly more precise detection of various constituents. Because the corresponding components are becoming less expensive, there is no obstacle to using a greater number of radiation sources, e.g., preferably LEDs.

The measurement device according to the invention includes at least one radiation source for irradiating the mixture in a number of definite, different wavelength ranges, at least one sensor for measuring the intensity of radiation that has been influenced by the mixture, and at least one set of measurement electronics. Although the electronics are described simply as measurement electronics, the term "measurement electronics" is intended to mean measurement and/or evaluation electronics. Each sensor detects only one of the definite, different wavelength ranges of the radiation at a particular time.

The process or the measurement device can, for example, be used in the sections of a pulp density regulated headbox of a paper machine. They can be used both in the diluted pulp range at pulp consistencies of approximately 2% and in the dense pulp range at pulp consistencies of approximately 2% to approximately 6% or more preferably 2.5% to 4.5%. They can also be used in inflows and/or outflows of a vat belonging to a paper machine and/or to part of a paper machine. In white water, a preferred consistency is between 0.01% and 0.4%. In a headbox, the consistency should be between 0.3% and 1.3%.

It is also advantageous to use the present invention in the region of the wet section of a paper machine. In this connection, the pulp consistencies can lie, for example, in a range of approximately 1% to approximately 30%. The measurement device according to the invention can, for example, also be used for the white water of a paper machine, where the pulp consistencies are as a rule considerably less than 1%, preferably between 0.01% and 0.4%.

For example, the beating degree, the air content, and/or the flocculation gradient in the mixture, which is constituted by a suspension, can be inferred from the respective measurement result. In this connection, the measurement electronics of the measurement device according to the invention can supply a respective signal that is representative of the relevant magnitude.

The present invention relates to a process for quantitatively detecting constituents of a pulp/fluid mixture for paper and cardboard production. The process includes irradiating the mixture with at least one radiation source, in which the irradiation occurring in a number of definite, different wavelength ranges, and measuring the intensity of radiation that has been influenced by the mixture by at least one sensor. Each sensor detects only one of the definite, different wavelength ranges of the radiation at a particular time.

According to another feature of the present invention, the process may further include detecting radiation, which has been reflected by the mixture, with at least one sensor.

According to still another feature of the present invention, the process may further include detecting radiation, which has passed through the mixture, with at least one sensor.

In accordance with another feature of the present invention, the process may further include irradiating the mixture by at least one optical radiation source, and measuring the intensity of the optical radiation that has been influenced by the mixture with at least one photoelectric transducer.

In a further feature of the present invention, the process may further include irradiating the mixture with a plurality of radiation sources, each radiation source having a different wavelength range. Further, the process may include irradiating the mixture in chronological sequence by at least one of the individual radiation sources having different wavelength ranges and by different combinations of radiation sources.

According to a still further feature of the present invention, the at least one sensor may include a wide band sensor that includes all of the different wavelength ranges.

In yet another feature of the present invention, the at least one radiation source may include at least one LED.

According to another feature of the present invention, the at least one sensor may include at least two sensors disposed at different distances from the radiation sources.

According to a further feature of the present invention, each radiation source may be respectively associated with one of a separate sensor and a separate sensor pair.

In accordance with a still further feature of the present invention, the at least one radiation source may include three optical radiation sources and the at least one sensor may include two sensors.

According to still another feature of the present invention, the at least one radiation source may include at least one of: at least one infrared LED, at least one red LED, and at least one blue LED. Further, the at least one LED may have an angle of radiation between approximately 12° and approximately 30°.

According to yet another feature of the present invention, the process may further include simultaneously measuring the intensity of optical radiation that has been influenced by the mixture and dielectricity, and quantitatively detecting constituents of the mixture using the measurement of the radiation intensity, the dielectricity measurement, and the ray absorption measurement. Measuring the dielectricity includes irradiating the mixture with microwave radiation.

In accordance with another feature of the present invention, the at least one sensor may include a plurality of sensors having different spectral sensitivities. The irradiating may include irradiating the mixture by a single radiation source.

In still another feature of the present invention, the at least one sensor may include a sensor/filter unit having at least one of an adjustable spectral sensitivity and an adjustable permeability.

According to a further feature of the present invention, the process may further include spectrally dividing the optical radiation that has been influenced by the mixture on the sensor end, and conveying the optical radiation to a photodiode array including at least 16 sensors.

The present invention also relates to a measurement device for quantitatively detecting constituents of a pulp/fluid mixture for paper and cardboard production. The measurement device includes at least one radiation source for irradiating the mixture in a plurality of definite, different wavelength ranges, at least one sensor for measuring the intensity of radiation that has been influenced by the mixture, and at least one set of measurement electronics. Each sensor detects only one of the definite, different wavelength ranges of the radiation at a particular time.

According to another feature of the present invention, the at least one sensor may detect radiation that has passed through the mixture.

According to another feature of the present invention, the at least one sensor may detect radiation that has been reflected by the mixture.

In accordance with still another feature of the present invention, at least one optical radiation source can irradiate the mixture, and at least one photoelectric transducer can measure the intensity of the optical radiation that has been influenced by the mixture.

In accordance with a further feature of the present invention, the at least one radiation source may include a plurality of radiation sources that irradiate the mixture, each radiation source having a different wavelength range. Further, the measurement electronics may include a system that sequentially irradiates the mixture by at least one of individual radiation sources having different wavelength ranges and different combinations of radiation sources.

In still a further feature of the present invention, the at least one sensor may include a wide band sensor that includes all of the different wavelength ranges.

According to yet another feature of the present invention, the at least one radiation source may include at least one LED.

In accordance with another feature of the present invention, the at least one sensor may include at least two sensors disposed at different distances from the at least one radiation source.

According to a further feature of the present invention, each radiation source may be respectively associated with one of a separate sensor and a separate sensor pair.

According to a still further feature of the present invention, the at least one radiation source may include three optical radiation sources, and the at least one sensor may include two sensors.

In still another feature of the present invention, the at least one sensor may include at least one of: at least one infrared LED, at least one red LED, and at least one blue LED.

According to another feature of the present invention, the at least one radiation source may include at least one LED having an angle of radiation lying in a range between approximately 12° and approximately 30°.

In accordance with another feature of the present invention, the at least one set of measurement electronics includes a system that simultaneously measures the intensity of optical radiation that has been influenced by the mixture and carries out a dielectricity measurement. The measurement of the radiation intensity, the dielectricity measurement, and the ray absorption are used for quantitatively detecting constituents of the mixture. Further, device may be provided for subjecting the mixture to microwave radiation for the dielectricity measurement.

In yet a further feature of the present invention, the at least one radiation source may include a single radiation source that irradiates the mixture, and the at least one sensor may include a plurality of sensors having different spectral sensitivities.

According to still another feature of the present invention, the at least one sensor may include at least one sensor/filter unit having at least one of adjustable spectral sensitivity and adjustable permeability.

In accordance with a still further feature of the present invention, a spectral divider may divide optical radiation that has been influenced by the mixture, and a photodiode array may be acted on by the divided radiation. The array may include at least 16 sensors.

According to yet another feature of the present invention, the measurement electronics may supply at least one signal that represents at least one of a beating degree, air content, and a flocculation gradient in the mixture, which is constituted by a suspension.

The present invention also relates to a process for quantitatively detecting constituents of a pulp/fluid mixture with an apparatus that includes at least one radiation source, at least one sensor, and at least one set of measurement electronics. The process includes positioning the apparatus in sections of a pulp density regulated headbox of a paper machine, irradiating the mixture in the sections with the at least one radiation source in a plurality of definite, different wavelength ranges, and measuring an intensity of the radiation that has been influenced by the mixture with the at least one sensor. The at least one sensor detects only one of the definite, different wavelength ranges of the radiation at a particular time.

The present invention also relates to a process for quantitatively detecting constituents of a pulp/fluid mixture with an apparatus that includes at least one radiation source, at least one sensor, and at least one set of measurement electronics. The process includes positioning the apparatus in at least one of inflows and outflows of a vat belonging to at least one of a paper machine and a part of a paper machine, irradiating the mixture in the at least one of the inflows and the outflows of the vat with the at least one radiation source in a plurality of definite, different wavelength ranges, and measuring an intensity of the radiation that has been influenced by the mixture with the at least one sensor. The at least one sensor detects only one of the definite, different wavelength ranges of the radiation at a particular time.

The present invention also relates to a process for quantitatively detecting constituents of a pulp/fluid mixture with an apparatus that includes at least one radiation source, at least one sensor, and at least one set of measurement electronics. The process includes positioning the apparatus in a region of a wet section of a paper machine, irradiating the mixture in the wet sections with the at least one radiation source in a plurality of definite, different wavelength ranges, and measuring an intensity of the radiation that has been influenced by the mixture with the at least one sensor. The at least one sensor detects only one of the definite, different wavelength ranges of the radiation at a particular time.

The present invention also relates to a process for quantitatively detecting constituents of a pulp/fluid mixture with an apparatus that includes at least one radiation source, at least one sensor, and at least one set of measurement electronics. The process includes positioning the apparatus for use in white water of a paper machine, irradiating the mixture in the white water with the at least one radiation source in a plurality of definite, different wavelength ranges, and measuring an intensity of the radiation that has been influenced by the mixture with the at least one sensor. The at least one sensor detects only one of the definite, different wavelength ranges of the radiation at a particular time.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
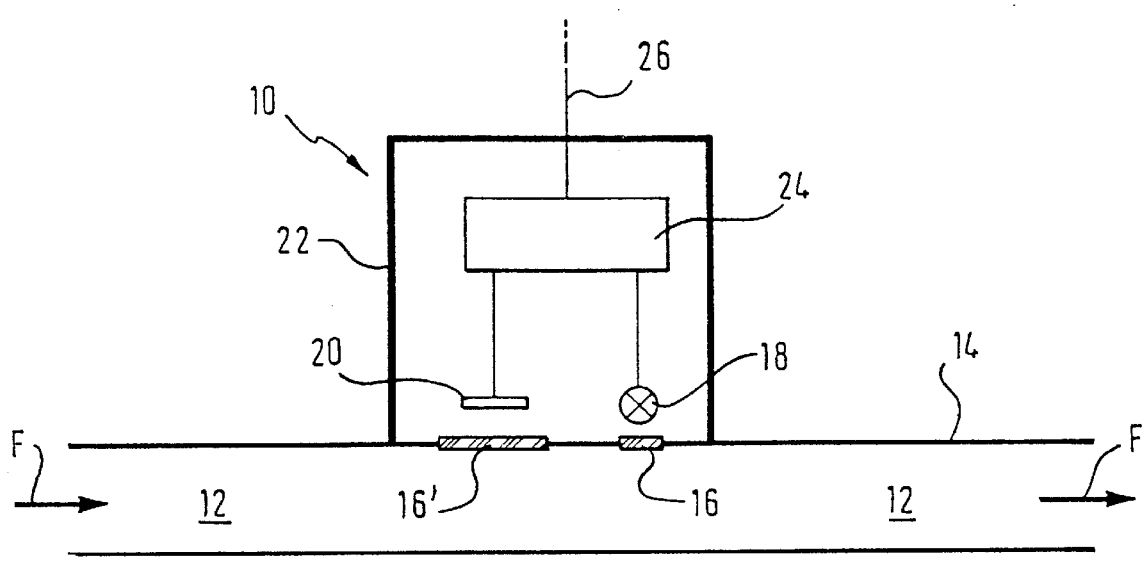
FIG. 1 is a schematic representation of a first embodiment of a measurement device for quantitative detection of constituents of a pulp/fluid mixture.

FIG. 1 is a schematic representation of a measurement device 10, which is used for quantitatively detecting constituents of a pulp/fluid mixture 12 for paper and/or cardboard production.

The measurement device 10 is disposed on a container of the mixture 12, which is constituted by a paper fiber suspension, in this instance a tube line 14. The mixture 12 flows in the direction of the arrows F past windows 16, 16' provided in the tube casing. The windows 16, 16' are disposed opposite at least one optical radiation source 18 such as an LED, or at least one sensor 20, such as a photoelectric transducer. The radiation sources 18 and the sensors 20 are disposed in the housing 22 of the measurement device 10. This sensor preferably comprises three LEDs, one blue, one red and one infrared LED. In addition, the sensor preferably comprises two photodiodes having an output of 0 to 10 volts.

Moreover, measurement electronics 24 are contained in the housing 22 of the measurement device 10, and are connected to the optical radiation sources 18 and the sensors 20. The measurement electronics 24 can be connected via at least one line 26 to a central system, in particular a process guidance system and/or a voltage supply. The electronics 24 control current to the LEDs, which is approximately 10 mA. The electronics also receive the signals from the photosensors and include a processor that calculates the consistency from the raw signals. The electronics are also capable of communicating with other computers.

The optical irradiation of the mixture 12 is carried out in a number of definite, different wavelength ranges. The intensity of the radiation that has been influenced by the mixture 12 is measured by at least one sensor 18. In this connection, each sensor 20 detects only one of the definite, different wavelength ranges of the radiation at a particular time. In the present exemplary embodiment, only the radiation that has been reflected by the mixture 12 is detected. Thus, the space requirement is reduced to a minimum.

Figure 2:
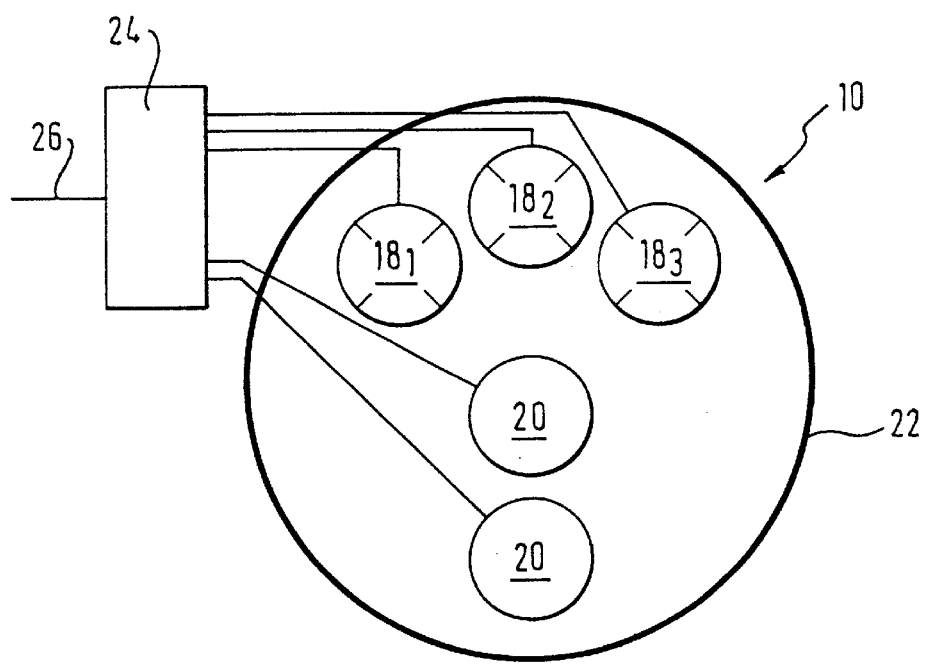
FIG. 2 is a schematic representation of another embodiment of the measurement device.

FIG. 2 is a schematic representation of a second embodiment of the measurement device 10 used for quantitatively detecting constituents. As can be seen from FIG. 2, the measurement device 10, which is once again provided with a housing 22, contains three optical radiation sources 18 and two sensors or photoelectric transducers 20. Both the radiation sources 18 and the sensors 20 are connected to the electronics 24, and the electronics can once again be connected via at least one line 26 to a control system, in particular a process guidance system and/or a voltage supply. According to this embodiment, the measurement electronics 24 are provided outside the housing 22.

In the second embodiment, the three optical radiation sources include an infrared LED $18_1$, a red LED $18_2$, and a blue LED $18_3$. The mixture is therefore irradiated by three radiation sources having different wavelength ranges. The two sensors or photoelectric transducers 20 are disposed at different distances from the radiation sources 18.

The measurement electronics 24 control the chronological sequence of the irradiation and measurement. They can, for example, be disposed on the housing 22 or, as in the second embodiment, accommodated in a separate housing. The measurement electronics 24 or a relevant control system can fundamentally supply at least one signal, which is representative, for example, of the beating degree, the air content, and/or the flocculation gradient in the mixture 12, which is in particular constituted by a suspension.

It is noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A process for quantitatively detecting constituents of a pulp/fluid mixture for paper and cardboard production, comprising:

irradiating the mixture with at least one radiation source, the irradiation occurring in a number of definite, different wavelength ranges;

measuring the intensity of radiation that has been influenced by the mixture by at least one sensor; and quantitatively detecting constituents of a pulp/fluid mixture, wherein each sensor detects only one of the definite, different wavelength ranges of the radiation at a particular time.

2. The process according to claim 1, further comprising detecting radiation, which has been reflected by the mixture, with at least one sensor.

3. The process according to claim 1, further comprising irradiating the mixture by at least one optical radiation source; and measuring the intensity of the optical radiation that has been influenced by the mixture with at least one photoelectric transducer.

4. The process according to claim 1, further comprising irradiating the mixture with a plurality of radiation sources, each radiation source having a different wavelength range.

5. The process according to claim 4, further comprising irradiating the mixture in chronological sequence by at least one of the individual radiation sources having different wavelength ranges and by different combinations of radiation sources.

6. The process according to claim 1, wherein the at least one sensor further comprises a wide band sensor that includes all of the different wavelength ranges.

7. The process according to claim 1, wherein the at least one radiation source further comprises at least one LED.

8. The process according to claim 1, wherein the at least one sensor comprises at least two sensors disposed at different distances from the radiation sources.

9. The process according to claim 1, wherein each radiation source is respectively associated with either a separate sensor or a separate sensor pair.

10. The process according to claim 1, wherein the at least one radiation source further comprises three optical radiation sources and the at least one sensor further comprises two sensors.

11. The process according to claim 1, wherein the at least one radiation source further comprises at least one of: at least one infrared LED, at least one red LED, and at least one blue LED.

12. The process according to claim 11, wherein the at least one LED has an angle of radiation between approximately 12° and approximately 30°.

13. The process according to claim 1, further comprising simultaneously measuring the intensity of optical radiation that has been influenced by the mixture and dielectricity; and quantitatively detecting constituents of the mixture using the measurement of the radiation intensity, the dielectricity measurement, and a ray absorption measurement.

14. The process according to claim 13, wherein the measuring of the dielectricity comprises irradiating the mixture with microwave radiation.

15. The process according to claim 1, wherein the at least one sensor further comprises a plurality of sensors having different spectral sensitivities, and wherein the irradiating further comprises irradiating the mixture by a single radiation source.

16. The process according to claim 1, wherein the at least one sensor further comprises a sensor/filter unit having at least one of an adjustable spectral sensitivity and an adjustable permeability.

17. The process according to claim 1, further comprising spectrally dividing the optical radiation that has been influenced by the mixture on the sensor end, and conveying the optical radiation to a photodiode array including at least 16 sensors.

18. A process for quantitatively detecting constituents of a pulp/fluid mixture for paper and cardboard production, comprising:

irradiating the mixture with at least one radiation source, the irradiation occurring in a number of definite, different wavelength ranges; and measuring the intensity of radiation that has been influenced by the mixture by at least one sensor; and detecting radiation, which has passed through the mixture, with at least one sensor to quantitatively detect constituents of the pulp/fluid mixture, wherein each sensor detects only one of the definite, different wavelength ranges of the radiation at a particular time.

19. A process for quantitatively detecting constituents of a pulp/fluid mixture with an apparatus that includes at least one radiation source for irradiating the mixture in a plurality of definite, different wavelength ranges, at least one sensor for measuring the intensity of radiation that has been influenced by the mixture, and at least one set of measurement electronics, the process comprising:

positioning the apparatus in sections of a pulp density regulated headbox of a paper machine;

irradiating the mixture in the sections with the at least one radiation source in a plurality of definite, different wavelength ranges; and measuring an intensity of the radiation that has been influenced by the mixture with the at least one sensor to quantitatively detect constituents of the pulp/fluid mixture, wherein the at least one sensor detects only one of the definite, different wavelength ranges of the radiation at a particular time.

20. A process for quantitatively detecting constituents of a pulp/fluid mixture with an apparatus that includes at least one radiation source for irradiating the mixture in a plurality of definite, different wavelength ranges, at least one sensor for measuring the intensity of radiation that has been influenced by the mixture, and at least one set of measurement electronics, the process comprising:

positioning the apparatus in at least one of inflows and outflows of a vat belonging to at least one of a paper machine and a part of a paper machine;

irradiating the mixture in the at least one of the inflows and the outflows of the vat with the at least one radiation source in a plurality of definite, different wavelength ranges; and measuring an intensity of the radiation that has been influenced by the mixture with the at least one sensor to quantitatively detect constituents of the pulp/fluid mixture, wherein the at least one sensor detects only one of the definite, different wavelength ranges of the radiation at a particular time.

21. A process for quantitatively detecting constituents of a pulp/fluid mixture with an apparatus that includes at least one radiation source for irradiating the mixture in a plurality of definite, different wavelength ranges, at least one sensor for measuring the intensity of radiation that has been influenced by the mixture, and at least one set of measurement electronics, the process comprising:

positioning the apparatus in a region of a wet section of a paper machine;

irradiating the mixture in the wet sections with the at least one radiation source in a plurality of definite, different wavelength ranges; and measuring an intensity of the radiation that has been influenced by the mixture with the at least one sensor to quantitatively detect constituents of the pulp/fluid mixture, wherein the at least one sensor detects only one of the definite, different wavelength ranges of the radiation at a particular time.

22. A process for quantitatively detecting constituents of a pulp/fluid mixture with an apparatus that includes at least one radiation source for irradiating the mixture in a plurality of definite, different wavelength ranges, at least one sensor for measuring the intensity of radiation that has been influenced by the mixture, and at least one set of measurement electronics, the process comprising:

positioning the apparatus for use in white water of a paper machine;

irradiating the mixture in the white water with the at least one radiation source in a plurality of definite, different wavelength ranges; and measuring an intensity of the radiation that has been influenced by the mixture with the at least one sensor to quantitatively detect constituents of the pulp/fluid mixture, wherein the at least one sensor detects only one of the definite, different wavelength ranges of the radiation at a particular time.

* * * * *